US008986215B2

(12) United States Patent
Masumoto

(10) Patent No.: US 8,986,215 B2
(45) Date of Patent: Mar. 24, 2015

(54) IMAGE PROCESSING APPARATUS, IMAGE PROCESSING METHOD, AND IMAGE PROCESSING PROGRAM

(75) Inventor: Jun Masumoto, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 34 days.

(21) Appl. No.: 13/231,413

(22) Filed: Sep. 13, 2011

(65) Prior Publication Data
US 2012/0065530 A1 Mar. 15, 2012

(30) Foreign Application Priority Data
Sep. 14, 2010 (JP) ................................. 2010-205334

(51) Int. Cl.
| A61B 5/04 | (2006.01) |
| G06T 7/00 | (2006.01) |
| G06T 7/60 | (2006.01) |
| A61B 6/00 | (2006.01) |
| A61B 6/03 | (2006.01) |

(52) U.S. Cl.
CPC .............. *G06T 7/0012* (2013.01); *G06T 7/602* (2013.01); *A61B 6/503* (2013.01); *A61B 6/5217* (2013.01); *G06T 2207/10072* (2013.01); *G06T 2207/30048* (2013.01); *A61B 6/03* (2013.01); *A61B 6/5288* (2013.01); *A61B 6/541* (2013.01)
USPC .......................................... 600/508; 382/131

(58) Field of Classification Search
USPC ........................ 600/508; 382/128, 130, 131
See application file for complete search history.

(56) References Cited

U.S. PATENT DOCUMENTS

| 8,059,876 B2 * | 11/2011 | Masumoto et al. ........... 382/128 |
| 2008/0312527 A1 * | 12/2008 | Masumoto et al. ........... 600/425 |
| 2009/0131788 A1 | 5/2009 | Settlemier et al. |

FOREIGN PATENT DOCUMENTS

JP 9-238932 A 9/1997

OTHER PUBLICATIONS

Truong, Quynh A., et al., "Quantitative Analysis of Intraventricular Dyssynchrony Using Wall Thickness by Multidetector Computed Tomography", JACC: Cardiovascular Imaging, Elsevier Inc., vol. 1, No. 6, Nov. 1, 2008, pp. 772-781.
Van Kriekinge, Serge D., et al., "Automatic Global and Regional Phase Analysis from Gated Myocardial Perfusion SPECT Imaging: Application to the Characterization of Ventricular Contraction in Patients with Left Bundle Branch Block", The Journal of Nuclear Medicine, Society of Nuclear Medicine and Molecular Imaging, vol. 49, No. 11, Oct. 16, 2008, pp. 1790-1797.
Chen, Ji., et al., "Assessment of Left Ventricular Mechanical Dyssynchrony by Phase Analysis of ECG-Gated SPECT Myocardial Perfusion Imaging", Journal of Nuclear Cardiology, vol. 15, No. 1, Jan. 30, 2008, pp. 127-136.

(Continued)

*Primary Examiner* — Eric D. Bertram
(74) *Attorney, Agent, or Firm* — Sughrue Mion, PLLC

(57) ABSTRACT

The systolic timings of myocardia at various positions of a heart are analyzed and evaluated. An image processing apparatus 1 obtains myocardial thicknesses at various positions of a heart within a plurality of three dimensional images V1 through VK, obtained by imaging a heart at a plurality of temporal phases within a single cardiac cycle, at each of the temporal phases. The image processing apparatus 1 obtains representative values that represent the systolic phase of the myocardia at each position, based on the obtained myocardial thicknesses at each temporal phase, and outputs the obtained representative values.

14 Claims, 4 Drawing Sheets

(56) References Cited

OTHER PUBLICATIONS

Sharir, Tali, et al., "Quantitative Analysis of Regional Motion and Thickening by Gated Myocardial Perfusion SPECT: Normal Heterogeneity and Criteria for Abnormality", The Journal of Nuclear Medicine, Society of Nuclear Medicine and Molecular Imaging, vol. 42, No. 11, Jan. 1, 2001, pp. 1630-1638.

Search Report, dated Apr. 22, 2014, issued by the European Patent Office in counterpart European Patent Application No. 11180919.0.

* cited by examiner

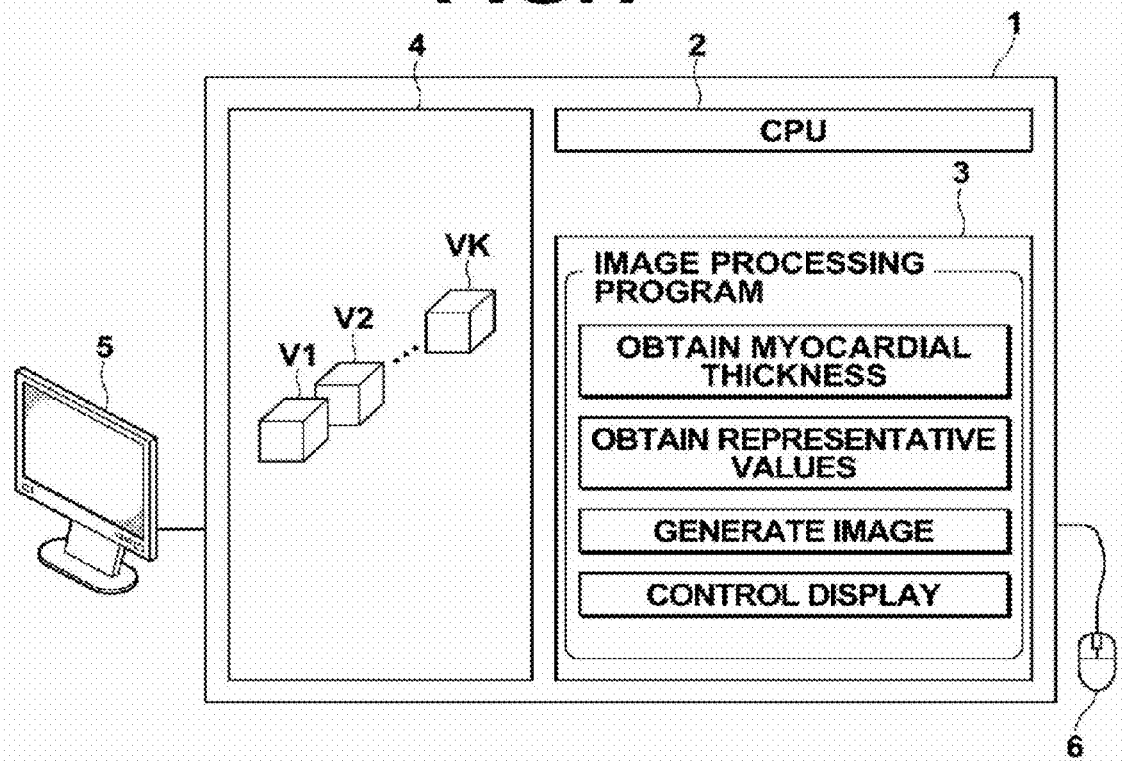
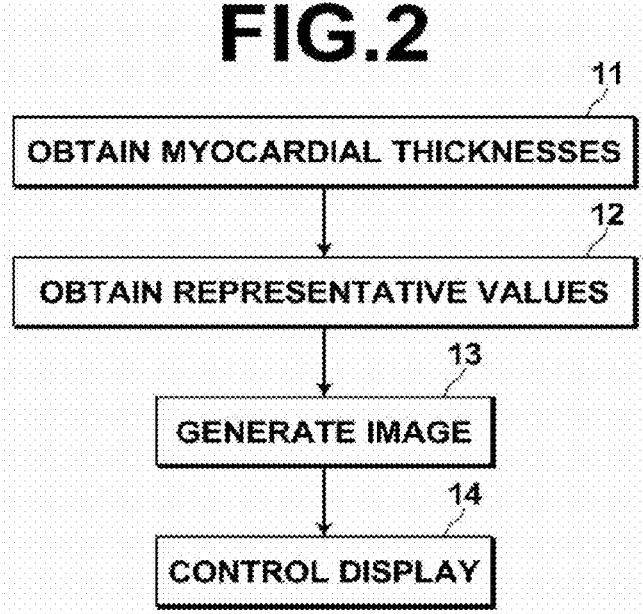

IMAGE PROCESSING APPARATUS, IMAGE PROCESSING METHOD, AND IMAGE PROCESSING PROGRAM

BACKGROUND OF THE INVENTION

1. Field of the Invention

The present invention is related to an image processing apparatus, an image processing method, and an image processing program for investigating states of cardiac motion.

2. Description of the Related Art

The heart pumps out blood, which is temporarily stored therein, to circulate the blood throughout the body by periodic contracting and expanding motions of myocardia. If circulation of blood deteriorates due to incomplete cardiac motion, immunity decreases, which is a factor that may cause various diseases.

In this respect, various methods for analyzing and evaluating states of cardiac motion have been proposed. For example, there is a known technique in which amounts of myocardial wall motion and changes in myocardial wall thickness are measured from a plurality of three dimensional images of a heart by imaging in temporal series, then the state of cardiac motion is evaluated employing the results of measurement. In addition, there is another known technique that evaluates the state of cardiac motion by a value obtained by dividing an amount of blood pumped by a single heartbeat (ejection amount) by the volume of a left ventricle (refer to Japanese Unexamined Patent Publication No. 9 (1997)-238932).

In hearts, contracting/expanding motions are not performed by all of the myocardia simultaneously, and the timings of contractions/expansions differ among parts of the heart. Particularly, a twisting motion of a specific pattern generated by the slight shifts in contraction timings enables efficient circulation of blood throughout the body. However, if changes occur in the contraction timings due to myocardial infarction or the like, efficient circulation of blood is precluded, which is a problem. Therefore there is demand to analyze and evaluate the contraction timings of myocardia at a plurality of positions of the heart.

However, the aforementioned conventional techniques do not focus on the shifts in the contraction timings of different parts of myocardia, and it cannot be said that they provide a solution to the above needs regarding analysis of cardiac motion.

SUMMARY OF THE INVENTION

The present invention has been developed in view of the foregoing circumstances. It is an object of the present invention to provide an image processing apparatus, an image processing method, and an image processing program capable of analyzing and evaluating the contraction timings of myocardia at each of a plurality of positions of the heart.

An image processing apparatus of the present invention is characterized by comprising:

image recording means, for recording a plurality of three dimensional images obtained by imaging a heart at a plurality of temporal phases during a single cardiac cycle;

myocardial thickness obtaining means, for obtaining the myocardial thicknesses at a plurality of positions of the heart at each of the temporal phases from the plurality of three dimensional images;

representative value obtaining means, for obtaining representative values that represent the systolic phase of the myocardia at each of the plurality of positions, based on the obtained myocardial thicknesses for each of the temporal phases; and output means, for outputting the obtained representative values.

Here, the term "outputting" refers to various forms of output, such as output to a data recording device (recording onto media), output to a display device (display on a monitor), output to a printer (printout), etc.

In the apparatus of the present invention, the output means may generate a representative value image that represents the representative values such that visual recognition of differences in the sizes of the representative values of each of the plurality of positions is enabled, and display the generated representative value image with a display means.

The representative value image may be an image that represents the three dimensional shape of the heart, in which colors correlated to the sizes of the representative values in advance are provided at pixels that represent the plurality of positions. Alternatively, the representative value image may be a bull's eye image, in which colors correlated to the sizes of the representative values in advance are provided at pixels that represent the plurality of positions.

Here, the expression "such that visual recognition of differences . . . is enabled" refers to expressing differences in the sizes of the representative values by different colors, textures, or the like in the displayed image.

The output means may display a three dimensional image obtained by imaging the heart or a two dimensional image that represents a cross section of the heart, in which colors correlated to the sizes of the representative values in advance are provided at pixels that represent the plurality of positions.

In the apparatus of the present invention, the representative values may be values that represent temporal phases at midpoints between temporal phases at which the myocardial thickness is maximal and temporal phases at which the myocardial thickness is minimal. Alternatively, the representative values may be values that represent temporal phases at which the myocardial thickness is maximal. As a further alternative, the representative values may be values that represent temporal phases at which the myocardial thickness is minimal.

As a still further alternative, the representative values may be values that represent the temporal phases at inflection points between a point at which the myocardial thickness is maximal and a point at which the myocardial thickness is minimal along a curve that represents changes in the myocardial thicknesses.

The apparatus of the present invention may further comprise:

reference representative value obtaining means, for obtaining reference representative values that represent the systolic phase of myocardia at positions of a healthy heart anatomically corresponding to the plurality of positions of the heart;

difference value obtaining means, for obtaining difference values between the representative values at each of the plurality of positions of the heart obtained by the representative value obtaining means and the reference representative values at each of the positions of the healthy heart anatomically corresponding to the plurality of positions; and second output means, for outputting the obtained difference values. In this case, the second output means may generate a difference value image that represents the difference values such that visual recognition of the sizes of the difference values of each of the plurality of positions is enabled, and display the generated difference value image with a display means.

The apparatus of the present invention may further comprise:

electrocardiogram obtaining means, for obtaining electrocardiograms of the heart for a single cardiac cycle; and normalizing means, for extracting predetermined feature points from the obtained electrocardiograms and employing the temporal phases of the extracted feature points to normalize the representative values obtained by the representative value obtaining means; and wherein:

the output means outputs the normalized representative values.

The apparatus of the present invention may further comprise:

volume curve obtaining means, for obtaining changes in the volume of the left ventricle during the single cardiac cycle as a volume curve; and normalizing means, for extracting predetermined feature points from the obtained volume curve and employing the temporal phases of the extracted feature points to normalize the representative values obtained by the representative value obtaining means; and wherein:

the output means outputs the normalized representative values.

An image processing method of the present invention is a method that causes at least one computer to execute the processes performed by the means of the image processing apparatus of the present invention.

An image processing program of the present invention is a program that causes at least one computer to execute the processes performed by the means of the image processing apparatus of the present invention. The program may be provided to users by being stored in recording media, such as CD-ROM's and DVD's, by being storage in a storage unit attached to a server computer in a downloadable state, or by being stored in network storage in a downloadable state.

The image processing apparatus, the image processing method, and the image processing program of the present invention obtains the myocardial thicknesses at a plurality of positions of the heart from a plurality of three dimensional images obtained by imaging the heart at a plurality of temporal phases within a single cardiac cycle. Representative values that represent the systolic phase of the myocardia are obtained for each of the plurality of positions, based on the myocardial thicknesses obtained for each temporal phase, then output. Thereby, users, such as physicians, can employ the representative values to easily analyze and evaluate the contraction timings of the myocardia at each of the plurality of positions of the heart.

In the image processing apparatus, the image processing method, and the image processing program of the present invention, the representative values may be output by generating a representative value image that represents the representative values such that visual recognition of differences in the sizes of the representative values of each of the plurality of positions is enabled, and displaying the generated representative value image with a display means. In this case, the display of the representative value image will enable users such as physicians to easily visually understand the contraction timings of the myocardia at each of the plurality of positions of the heart.

In addition, reference representative values that represent the systolic phase of myocardia may be obtained for positions of a healthy heart anatomically corresponding to the plurality of positions of the heart; difference values between the representative values at each of the plurality of positions of the heart obtained by the representative value obtaining means and the reference representative values at each of the positions of the healthy heart may be obtained; and the obtained difference values may be output. In this case, users, such as physicians, can employ the difference values to easily analyze and evaluate the differences between contraction timings of the myocardia at each of the plurality of positions of the heart from those of a healthy heart.

Further, a difference value image that represents the difference values such that visual recognition of the sizes of the difference values of each of the plurality of positions is enabled may be generated, and the generated difference value image may be displayed with a display means. In this case, the display of the difference value image will enable users such as physicians to easily visually understand the differences between contraction timings of the myocardia at each of the plurality of positions of the heart from those of a healthy heart.

Still further, feature points may be extracted from electrocardiograms or volume curves that represent the changes in the volume of the left ventricle during a single cardiac cycle, the temporal phases of the extracted feature points may be employed to normalize the obtained representative values, and the normalized representative values may be output. In this case, users such as physicians can easily compare the representative values of a heart against those of a healthy heart, or those of other hearts.

BRIEF DESCRIPTION OF THE DRAWINGS

FIG. 1 is a diagram that schematically illustrates the configuration of an image processing apparatus of the present invention.

FIG. 2 is a diagram that schematically illustrates the processes executed by the image processing apparatus.

DESCRIPTION OF THE PREFERRED EMBODIMENTS

Figure 3:
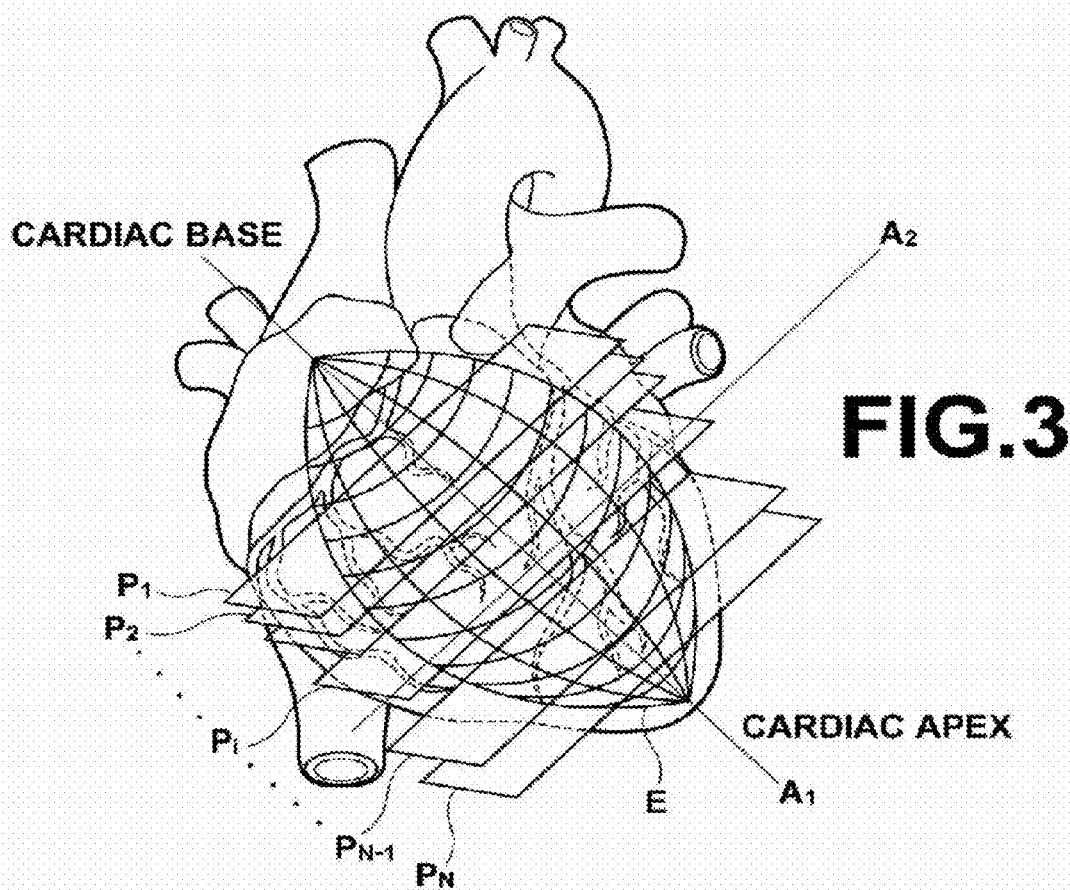
FIG. 3 is a diagram for explaining a myocardial thickness obtaining process.

Hereinafter, embodiments of the image processing apparatus, the image processing method, and the image processing program of the present invention will be described in detail with reference to the attached drawings.

The image processing apparatus 1 of the present invention is a single computer, in which an image processing program is installed. The computer may be a workstation or a personal computer which is directly operated by a physician that performs diagnosis. Alternatively, the computer may be a server computer connected to such a workstation or a personal computer. The image processing program is distributed stored in a recording medium such as a DVD and a CD-ROM, and installed in the computer from the recording medium. Alternatively, the image processing program is recorded in a storage unit attached to the server computer or recorded in network storage such that it is accessible from the exterior, downloaded to the computer utilized by the physician upon request, and installed therein.

FIG. 1 is a diagram that schematically illustrates the configuration of the image processing apparatus 1, realized by installing the image processing program in a workstation. As illustrated in FIG. 1, the image processing apparatus 1 is equipped with a CPU 2, a memory 3, and a storage 4, as a standard configuration of a workstation. In addition, a display 5, and input devices, such as a mouse 6, are connected to the image processing apparatus 1.

A series of three dimensional images V1 through VK, which are obtained by imaging a heart at a plurality of temporal phases t1 through tK during a single cardiac cycle T, are stored in the storage 4. The three dimensional images V1 through VK are generated by reconstructing pluralities of tomographic images obtained by a CT apparatus, an MRI apparatus, an ultrasound diagnostic apparatus, etc. Generally, three dimensional images corresponding to 10 to 20 phases are obtained during a single cardiac cycle T in electrocardiogram synchronized imaging of the heart. Therefore, it is normal for the number K of the three dimensional images V1 through VK to be within a range from 10 to 20.

In addition, the image processing program and data referred to by the image processing program (processing parameters, etc.) are stored in the memory 3. The image processing program defines a myocardial thickness obtaining process, a representative value obtaining process, an image generating process, and a display control process as processes to be executed by the CPU 2. The CPU 2 executes these processes according to the program, thereby causing the general purpose workstation to function as a myocardial thickness obtaining means, a representative value obtaining means, an image generating means, and a display control means.

FIG. 2 is a block diagram that schematically illustrates the processes executed by the image processing apparatus. The image processing apparatus 1 first loads the three dimensional images V1 through VK from the storage 4 to the memory 3. Then, the image processing apparatus 1 executes a myocardial thickness obtaining process 11 that obtains myocardial thicknesses at a plurality of positions of the heart for each of the temporal phases t1 through tK.

In the myocardial thickness obtaining process 11, the image processing apparatus 1 first extracts the left ventricle region from the three dimensional image V1. Then, the image processing apparatus 1 sets a long axis A1 that connects the base of the heart, the apex of the heart, and the center of the left ventricle, then sets a short axis A2 that perpendicularly intersects the long axis A1. Here, the long axis A1 is set by setting a plurality of cross sections that perpendicularly intersect a preliminarily set long axis, obtaining the positions of the barycenters of the left ventricle in the cross sectional images, and connecting the barycenters. Note that the long axis A1 may be set by approximating the extracted left ventricle region to the oval shaped surface model E illustrated in FIG. 3, and setting the long axis of the approximated model as the long axis A1.

Here, the left ventricle region is specified by determining the outline thereof. Specifically, the image processing apparatus 1 calculates features that represent likeliness of being the outline of the heart and features that represent likeliness of being the outline of the left ventricle from the values of voxel data that constitute the three dimensional image V1. Then, the calculated features are evaluated using evaluations functions which are obtained in advance by machine learning, and judgments are made regarding whether the voxel data represents the outline of the heart, and whether the voxel data represents the outline of the left ventricle. Voxel data that represent the outline of the entire heart and voxel data that represent the outline of the left ventricle are extracted by repeating these judgments. In the present embodiment, the Adaboost algorithm is employed to obtain the evaluation functions. Note that the extraction of the cardiac region may be performed by other machine learning methods or statistical analysis methods, such as the linear judgment method, neural networks, and support vector machines.

Figure 4:
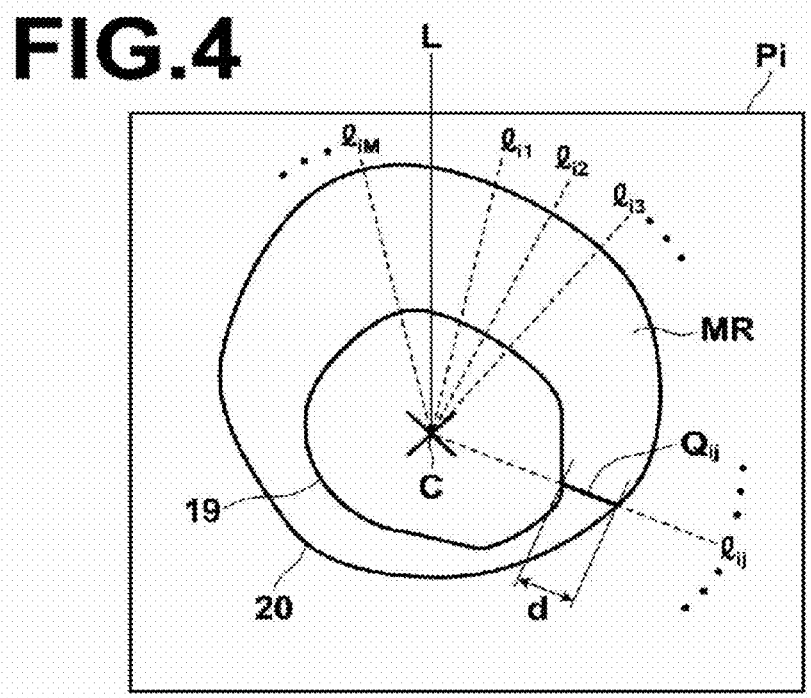
FIG. 4 is a diagram for explaining a myocardial thickness obtaining process.

Next, a plurality of cross sections Pi (i=1 through N) that perpendicularly intersect with the long axis A1 are set. Then, an outline 19 of the endocardium and an outline 20 of the epicardium are extracted within each cross section Pi, as illustrated in FIG. 4. Then, the lengths of line segments Qij, which are segments of lines Lij (j=1 through M) that extend radially outward from a point C through which the long axis A1 passes within each cross section Pi between the outline 19 of the endocardium and the outline 20 of the epicardium, are obtained as a length d of the myocardium at that position. The thicknesses of the myocardia at each position (i, j) of the heart at temporal phase t1 are obtained in this manner.

Thereafter, the positions of anatomically corresponding points of the heart within the three dimensional images V1 through VK are obtained, by positionally aligning the three dimensional images V1 through VK. Specifically, the positions of anatomically corresponding points within three dimensional images of two sequential temporal phases are obtained, by positionally aligning these three dimensional images such that the pixel values thereof match. Further, positional alignment of three dimensional images of two or more temporal phases is sequentially performed along the passage of time. Thereby, the positions of anatomically corresponding points are obtained within three dimensional images of two or more temporal phases.

The positional alignment may be performed by arranging B spline control points at constant intervals within a three dimensional space, and moving the control points to deform the three dimensional space such that the shapes of hearts within three dimensional images of two sequential temporal phases are matched. Note that details of a method for positionally aligning three dimensional images by deforming three dimensional spaces are described in U.S. Patent Application Publication No. 20080312527, for example.

Next, positional data regarding each of the aforementioned corresponding points are employed to specify the positions of linear regions within the three dimensional image V2 that anatomically correspond to the line segments Qij within the three dimensional image V1. Then, the lengths of the linear regions are obtained as the thicknesses d of the myocardia at each position (i, j) for temporal phase t2. Thereafter, the same processes are repeated for the three dimensional images V3 through VK, to obtain the myocardial thicknesses d at each position (i, j) for the temporal phase t3 through tK. Note that the lengths of the specified linear regions are measured along the trajectories thereof.

Note that a case has been described in which the positions of the same portions of the myocardia at each temporal phase are tracked by positionally aligning the three dimensional images V1 through VK, and the thicknesses at these positions are obtained. However, the present invention is not limited to such a configuration. For example, positional alignment need not be performed among images, and the same process as that performed to obtain the myocardial thicknesses from the three dimensional image V1 may be performed on the three dimensional images V2 through VK instead, to obtain the myocardial thicknesses at each of the temporal phases t2 through tK. Specifically, the long axis, the short axis, the cross sections, and the radial line segments are set for each of the three dimensional images V2 through VK in the same manner as that for the three dimensional image V1, and the lengths of the radial line segments that pass through the myocardial regions are obtained as the thicknesses of the myocardia.

Figure 5:
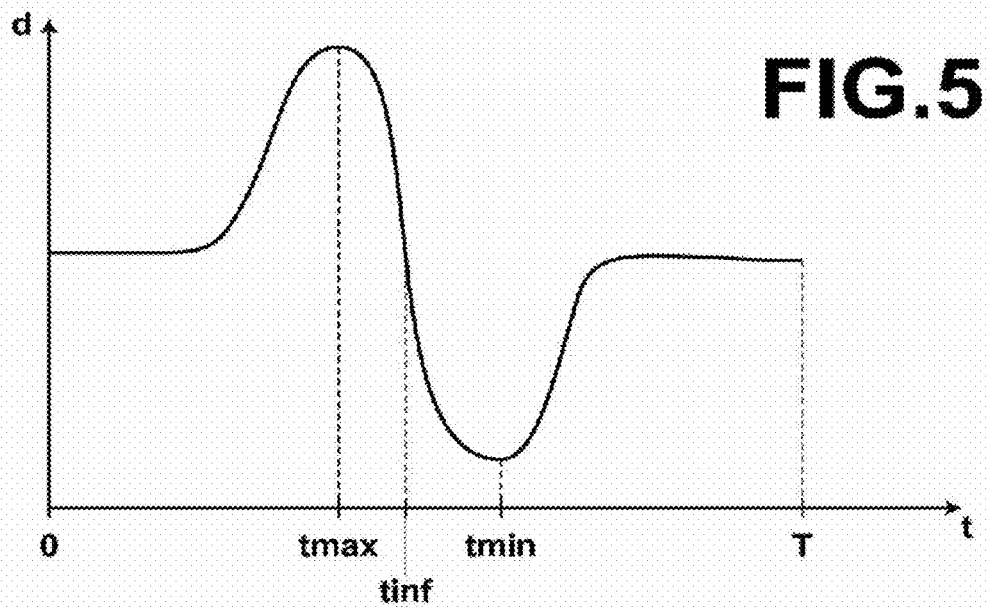
FIG. 5 is a diagram for explaining a representative value obtaining process.

The image processing apparatus 1 next executes a representative value obtaining process 12. In the representative value obtaining process 12, representative values that represent the systolic phase of the myocardia at each of the positions (i, j) are obtained, based on the myocardial thicknesses d obtained by the myocardial thickness obtaining process 11. Specifically, values that represent temporal phases (tmax+tmin/2) at the midpoints between temporal phases (tmax) at which the myocardial thickness is maximal and temporal phases (tmin) at which the myocardial thickness is minimal in graphs that indicate changes in myocardial thicknesses at predetermined positions within the single cardiac cycle T, such as that illustrated in FIG. 5, are obtained as the representative values at these positions.

Note that here, a case has been described in which values that represent temporal phases (tmax+tmin/2) at the midpoints between temporal phases (tmax) at which the myocardial thickness is maximal and temporal phases (train) at which the myocardial thickness is minimal are obtained as the representative values. However, the representative values may be values that represent temporal phases (tmax) at which the myocardial thickness is maximal, values that represent temporal phases (thin) at which the myocardial thickness is minimal, or values that represent temporal phases (tinf) at inflection points between a point at which the myocardial thickness is maximal and a point at which the myocardial thickness is minimal.

Next, the image processing apparatus 1 executes an image generating process 13. In the image generating process 13, a representative value image is generated that expresses differences in the sizes of the representative values at each of the positions (i, j) of the heart obtained by the representative value obtaining process 12 such that the differences are visually recognizable.

Figure 6:
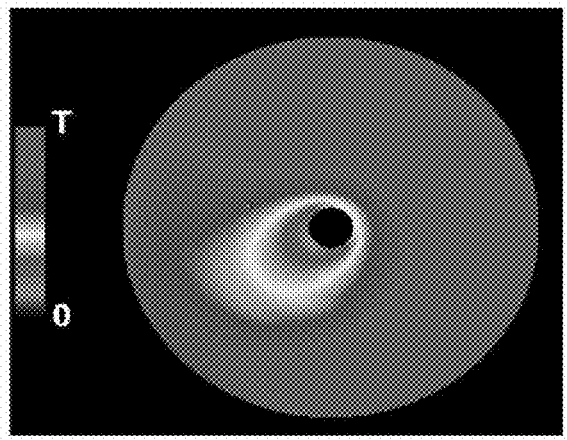
FIG. 6 is a diagram that illustrates a first example of a representative value image.

Specifically, a bulls eye image, in which the representative values at each position in a cross section closest to the apex of the heart are arranged along a circle having the smallest radius, and the representative values at each position in a cross section furthest from the apex of the heart are arranged along a circle having the largest radius, is generated, as illustrated in FIG. 6. In this bull's eye image, colors which are correlated in advance to the sizes of the representative values are provided at pixels that represent each position of the heart within the image. The color bar at the left of FIG. 6 indicates the correspondent relationship between colors and the representative values. The generated bull's eye image is stored in the memory 3, and is utilized in a display control process 14 to be described later.

Figure 7:
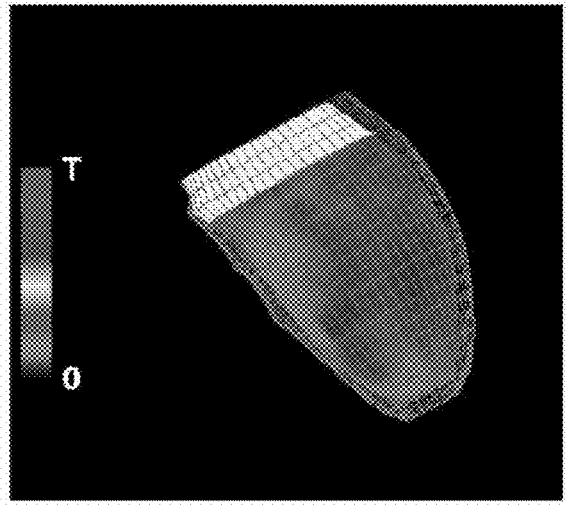
FIG. 7 is a diagram that illustrates a second example of a representative value image.
Figure 8:
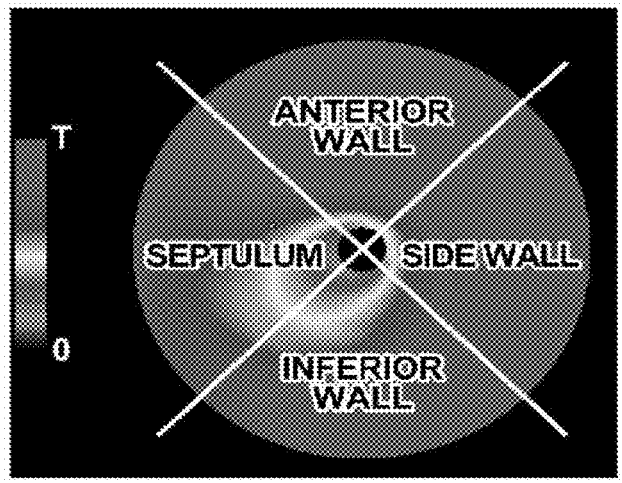
FIG. 8 is a diagram for explaining a method by which a representative value image is generated.
Figure 9:
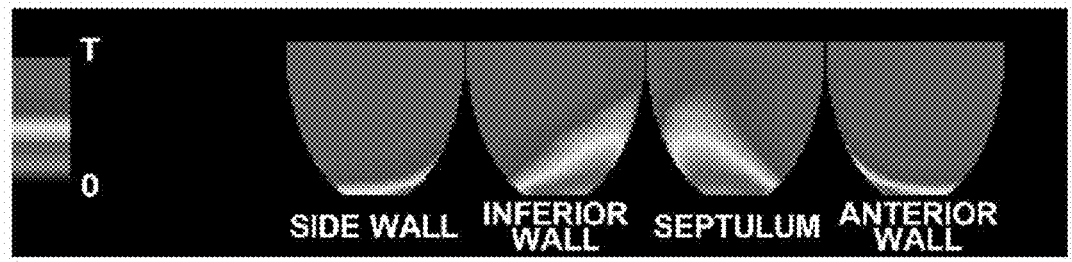
FIG. 9 is a diagram that illustrates a third example of a representative value image.

Note that here, a case has been described in which the bull's eye image is generated as an example of the representative value image. Alternatively, an image that represents the three dimensional shape of the heart may be generated, in which colors which are correlated in advance to the sizes of the representative values are provided at pixels that represent each position of the heart within the image, as illustrated in FIG. 7. In addition, coordinate axes of the bulls eye image may be quartered as illustrated in FIG. 8, and a topographic map such as that illustrated in FIG. 9 may be generated as the representative value image.

Figure 10:
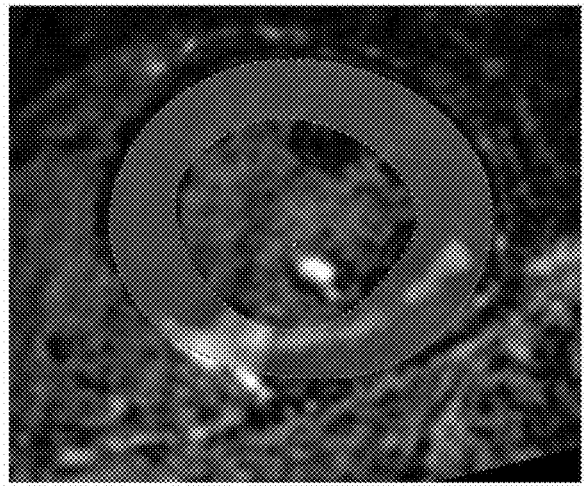
FIG. 10 is a diagram that illustrates a fourth example of a representative value image.

As a further alternative, a two dimensional image that displays a single cross sectional surface of the heart may be generated, in which colors which are correlated in advance to the sizes of the representative values are provided at pixels that represent each position of the heart within the image, as illustrated in FIG. 10.

Next, the image processing apparatus 1 executes a display control process 14 that displays the representative value image stored in the memory 3 on the display 5 according to a request from the user.

As described above, the image processing apparatus, the image of the present embodiment obtains the myocardial thicknesses d at a plurality of positions of the heart from a plurality of three dimensional images V1 through VK obtained by imaging the heart at a plurality of temporal phases t1 through tK within a single cardiac cycle T. Representative values that represent the systolic phase of the myocardia are obtained for each of the plurality of positions, based on the myocardial thicknesses obtained for each temporal phase, then output. Thereby, users, such as physicians, can employ the representative values to easily analyze and evaluate the contraction timings of the myocardia at each of the plurality of positions of the heart.

In addition, the image processing apparatus 1 generates the representative value image that represents the representative values such that visual recognition of differences in the sizes of the representative values of each of the plurality of positions is enabled, and displays the generated representative value image on the display 5. The display of the representative value image enables users such as physicians to easily visually understand the contraction timings of the myocardia at each of the plurality of positions of the heart.

Note that the image processing apparatus 1 may further execute a normalizing process that normalizes the representative values obtained by the representative value obtaining process 12, and may execute the image generating process 13 and the display control process 14 using the normalized representative values.

The normalizing process employs the temporal phase of a Q point from among PQRST waves of an electrocardiogram of the signal cardiac cycle T obtained in synchronization with the imaging of the three dimensional images V1 through VK as a feature point. Then, the representative values are normalized by sliding deformation of the temporal axis of the cardiac cycle T such that the feature point matches a reference value which is set in advance. Here, average value of the temporal phases of Q points obtained from electrocardiograms of a great number of healthy hearts may be employed as the reference value. Note that the normalization process may be that in which the representative values are normalized, by designating the temporal phases of R points and S points from among PQRST waves as feature points, and the temporal axis of the single cardiac cycle T is expanded/contracted such that the interval between the temporal phases match a reference value set in advance. In this case, an average value of intervals between the temporal phases of R points and S points obtained from electrocardiograms of a great number of healthy hearts may be employed as the reference value.

The normalizing process may be performed employing an EF curve (a graph that represents changes in the volume of the left ventricle) instead of the electrocardiogram. Predetermined feature points are extracted from the EF curve obtained in synchronization with the imaging of the three dimensional images V1 through VK, and the temporal axis within the single cardiac cycle is deformed such that the temporal phases of the extracted feature points match predetermined reference values.

Further, the image processing apparatus 1 may execute a process that obtains difference values between each of the representative values obtained by the representative value obtaining process 12 and reference representative values of a healthy heart, which are obtained in advance, and a process that outputs the obtained difference values. Note that the difference values may be output in the same manners as the representative values. For example, the image generating process 13 and the display control process 14 described previously may be applied to generate a bulls eye image, a topographic map, etc., that represent the difference values obtained for each position of the heart and to display the generated image on the display 5.

The reference representative values of the healthy heart may be obtained by the following method. First, the myocardial thickness obtaining process 11 and the representative value obtaining process 12 are administered on series of three dimensional images obtained by imaging a great number of hearts, which are known to be healthy, in a single cardiac cycle. Thereby, the representative values for each position of the healthy hearts are obtained. Then, the normalizing process described above is administered on the obtained representative values. Next, the images that represent the healthy hearts are positionally aligned, to obtain the positions of corresponding points. Then, average values of the representative values obtained for each of the healthy hearts are calculated at each of the plurality of positions, and the calculated average values are designated as the reference representative values at each of the positions.

What is claimed is:

1. An image processing apparatus, comprising:
    image recording means, for recording a plurality of three dimensional images obtained by imaging a heart at a plurality of temporal phases during a single cardiac cycle;
    myocardial thickness obtaining means, for obtaining the myocardial thicknesses at a plurality of positions of the heart at each of the temporal phases from the plurality of three dimensional images;
    representative value obtaining means, for obtaining representative values that represent the contraction timings of the myocardia at each of the plurality of positions, based on the obtained myocardial thicknesses for each of the temporal phases; and
    output means, for outputting the obtained representative values, wherein:
    the output means generates a representative value image that represents the representative values such that visual recognition of differences in the sizes of the representative values of each of the plurality of positions is enabled, and displays the generated representative value image with a display means;
    the representative values are values that represent temporal phases at which the myocardial thickness is maximal.

2. An image processing apparatus as defined in claim 1, wherein:
    the representative value image is an image that represents the three dimensional shape of the heart, in which colors correlated to the sizes of the representative values in advance are provided at pixels that represent the plurality of positions.

3. An image processing apparatus as defined in claim 1, wherein:
    the representative value image is a bull's eye image, in which colors correlated to the sizes of the representative values in advance are provided at pixels that represent the plurality of positions.

4. An image processing apparatus as defined in claim 1, further comprising:
    reference representative value obtaining means, for obtaining reference representative values that represent the systolic phase of myocardia at positions of a healthy heart anatomically corresponding to the plurality of positions of the heart;
    difference value obtaining means, for obtaining difference values between the representative values at each of the plurality of positions of the heart obtained by the representative value obtaining means and the reference representative values at each of the positions of the healthy heart anatomically corresponding to the plurality of positions; and
    second output means, for outputting the obtained difference values.

5. An image processing apparatus as defined in claim 4, wherein:
    the second output means generates a difference value image that represents the difference values such that visual recognition of the sizes of the difference values of each of the plurality of positions is enabled, and displays the generated difference value image with a display means.

6. An image processing apparatus as defined in claim 1, further comprising:
    electrocardiogram obtaining means, for obtaining electrocardiograms of the heart for a single cardiac cycle; and
    normalizing means, for extracting predetermined feature points from the obtained electrocardiograms and employing the temporal phases of the extracted feature points to normalize the representative values obtained by the representative value obtaining means; and wherein:
    the output means outputs the normalized representative values.

7. An image processing apparatus as defined in claim 1, further comprising:
    volume curve obtaining means, for obtaining changes in the volume of the left ventricle during the single cardiac cycle as a volume curve; and
    normalizing means, for extracting predetermined feature points from the obtained volume curve and employing the temporal phases of the extracted feature points to normalize the representative values obtained by the representative value obtaining means; and wherein:
    the output means outputs the normalized representative values.

8. An image processing apparatus as defined in claim 1, further comprising:
    reference representative value obtaining means, for obtaining reference representative values that represent the systolic phase of myocardia at positions of a healthy heart anatomically corresponding to the plurality of positions of the heart;
    difference value obtaining means, for obtaining difference values between the representative values at each of the plurality of positions of the heart obtained by the representative value obtaining means and the reference representative values at each of the positions of the healthy heart anatomically corresponding to the plurality of positions; and
    second output means, for outputting the obtained difference values.

9. An image processing apparatus as defined in claim 8, wherein:

the second output means generates a difference value image that represents the difference values such that visual recognition of the sizes of the difference values of each of the plurality of positions is enabled, and displays the generated difference value image with a display means.

10. An image processing method, comprising:

reading out a plurality of three dimensional images obtained by imaging a heart at a plurality of temporal phases during a single cardiac cycle from a recording medium in which the plurality of three dimensional images are stored;

obtaining the myocardial thicknesses at a plurality of positions of the heart at each of the temporal phases from the plurality of three dimensional images;

obtaining representative values that represent the contraction timings of the myocardia at each of the plurality of positions, based on the obtained myocardial thicknesses for each of the temporal phases; and outputting the obtained representative values, wherein:

the outputting step includes generating a representative value image that represents the representative values such that visual recognition of differences in the sizes of the representative values of each of the plurality of positions is enabled, and displaying the generated representative value image with a display means;

the representative values are values that represent temporal phases at which the myocardial thickness is maximal.

11. A non transitory computer readable recording medium, in which a program is recorded, the program causing a computer to function as:

image recording means, for recording a plurality of three dimensional images obtained by imaging a heart at a plurality of temporal phases during a single cardiac cycle;

myocardial thickness obtaining means, for obtaining the myocardial thicknesses at a plurality of positions of the heart at each of the temporal phases from the plurality of three dimensional images;

representative value obtaining means, for obtaining representative values that represent the contraction timings of the myocardia at each of the plurality of positions, based on the obtained myocardial thicknesses for each of the temporal phases; and output means, for outputting the obtained representative values, wherein:

the output means generates a representative value image that represents the representative values such that visual recognition of differences in the sizes of the representative values of each of the plurality of positions is enabled, and displays the generated representative value image with a display means;

the representative values are values that represent temporal phases at which the myocardial thickness is maximal.

12. An image processing apparatus, comprising:

image recording means, for recording a plurality of three dimensional images obtained by imaging a heart at a plurality of temporal phases during a single cardiac cycle;

myocardial thickness obtaining means, for obtaining the myocardial thicknesses at a plurality of positions of the heart at each of the temporal phases from the plurality of three dimensional images;

representative value obtaining means, for obtaining representative values that represent the contraction timings of the myocardia at each of the plurality of positions, based on the obtained myocardial thicknesses for each of the temporal phases; and output means, for outputting the obtained representative values, wherein:

the output means generates a representative value image that represents the representative values such that visual recognition of differences in the sizes of the representative values of each of the plurality of positions is enabled, and displays the generated representative value image with a display means; and the representative values are values that represent the temporal phases at inflection points between a point at which the myocardial thickness is maximal and a point at which the myocardial thickness is minimal along a curve that represents changes in the myocardial thicknesses.

13. An image processing method, comprising:

reading out a plurality of three dimensional images obtained by imaging a heart at a plurality of temporal phases during a single cardiac cycle from a recording medium in which the plurality of three dimensional images are stored;

obtaining the myocardial thicknesses at a plurality of positions of the heart at each of the temporal phases from the plurality of three dimensional images;

obtaining representative values that represent the contraction timings of the myocardia at each of the plurality of positions, based on the obtained myocardial thicknesses for each of the temporal phases; and outputting the obtained representative values, wherein:

the outputting step includes generating a representative value image that represents the representative values such that visual recognition of differences in the sizes of the representative values of each of the plurality of positions is enabled, and displaying the generated representative value image with a display means; and the representative values are values that represent the temporal phases at inflection points between a point at which the myocardial thickness is maximal and a point at which the myocardial thickness is minimal along a curve that represents changes in the myocardial thicknesses.

14. A non transitory computer readable recording medium, in which a program is recorded, the program causing a computer to function as:

image recording means, for recording a plurality of three dimensional images obtained by imaging a heart at a plurality of temporal phases during a single cardiac cycle;

myocardial thickness obtaining means, for obtaining the myocardial thicknesses at a plurality of positions of the heart at each of the temporal phases from the plurality of three dimensional images;

representative value obtaining means, for obtaining representative values that represent the contraction timings of the myocardia at each of the plurality of positions, based on the obtained myocardial thicknesses for each of the temporal phases; and output means, for outputting the obtained representative values, wherein:

the output means generates a representative value image that represents the representative values such that visual recognition of differences in the sizes of the representative values of each of the plurality of positions is enabled, and displays the generated representative value image with a display means; and the representative values are values that represent the temporal phases at inflection points between a point at which the myocardial thickness is maximal and a point at which the myocardial thickness is minimal along a curve that represents changes in the myocardial thicknesses.

\* \* \* \* \*